[12] United States Patent
Syage et al.

(10) Patent No.: US 9,354,153 B2
(45) Date of Patent: May 31, 2016

(54) HAND-HELD TRACE PARTICLE SAMPLING SYSTEM AND METHOD OF OPERATING THE SAME

(71) Applicant: Morpho Detection, LLC, Newark, CA (US)

(72) Inventors: Jack A. Syage, Huntington Beach, CA (US); Karl A. Hanold, Huntington Beach, CA (US)

(73) Assignee: MORPHO DETECTION, LLC, Newark, CA (US)

(*) Notice: Subject to any disclaimer, the term of this patent is extended or adjusted under 35 U.S.C. 154(b) by 481 days.

(21) Appl. No.: 13/843,320

(22) Filed: Mar. 15, 2013

(65) Prior Publication Data

US 2015/0268147 A1 Sep. 24, 2015

Related U.S. Application Data

(60) Continuation-in-part of application No. 11/639,579, filed on Dec. 15, 2006, now Pat. No. 8,434,375, which is a division of application No. 11/202,455, filed on Aug. 11, 2005, now Pat. No. 7,299,710.

(51) Int. Cl.
*G01N 1/22* (2006.01)
*G01N 15/02* (2006.01)

(52) U.S. Cl.
CPC .......... *G01N 15/0255* (2013.01); *G01N 1/2208* (2013.01); *G01N 1/2273* (2013.01); *G01N 2015/0261* (2013.01)

(58) Field of Classification Search
None
See application file for complete search history.

(56) References Cited

U.S. PATENT DOCUMENTS

| 3,362,141 | A * | 1/1968 | Royster, Jr. ............. G01N 1/04 55/468 |
| 6,101,886 | A * | 8/2000 | Brenizer et al. ........... 73/863.23 |
| 7,135,060 | B2 * | 11/2006 | Jordan et al. ................ 96/413 |
| 7,141,786 | B2 * | 11/2006 | McGann et al. ............. 250/287 |
| 7,275,453 | B2 * | 10/2007 | Ishikawa et al. ........... 73/864.33 |
| 7,799,567 | B1 | 9/2010 | Call |
| 2004/0094707 | A1 | 5/2004 | Jenkins et al. |
| 2009/0223310 | A1 | 9/2009 | Syage et al. |
| 2011/0186436 | A1 | 8/2011 | Novosselov et al. |
| 2011/0203931 | A1 * | 8/2011 | Novosselov et al. .......... 204/600 |
| 2014/0060213 | A1 * | 3/2014 | Uang et al. ................. 73/863.22 |

FOREIGN PATENT DOCUMENTS

EP 1517129 A2 3/2005

OTHER PUBLICATIONS

Canadian Office Action, dated May 27, 2014, for co-pending Canadian patent application No. 2688352 (2 pgs.).
Communication Pursuant to Article 94(3) EPC from the European Patent Office, dated Apr. 24, 2015, for co-pending EP application No. EP 06 851 631.9 (7 pgs.).

(Continued)

*Primary Examiner* — Robert R Raevis
(74) *Attorney, Agent, or Firm* — Armstrong Teasdale LLP

(57) ABSTRACT

A particle impact device for a hand-held trace particle detection system includes an intake manifold that includes a first conduit defining an intake port. The intake port defines a first transport area. The intake manifold also includes a second conduit coupled to the first conduit. The second conduit defines a discharge port that defines a second transport area. The first transport area is greater than the second transport area. The particle impact device also includes a combined deposition and deflection apparatus positioned downstream of the discharge port. The combined deposition and deflection apparatus defines a deposition and deflection surface positioned a predetermined distance from the discharge port. The deposition and deflection surface is configured to deflect a fluid stream and collect at least a portion of particles entrained in the fluid stream.

19 Claims, 13 Drawing Sheets

(56) References Cited

OTHER PUBLICATIONS

First Office Action from the European Patent Office, dated Apr. 24, 2015, for co-pending EP patent application No. EP 09 739 408.4 (6 pgs.).

Extended European Search Report, dated Mar. 18, 2016, for European patent application No. EP 14000785.7 (9 pgs.).

European Office Action, dated Feb. 18, 2016, for European patent application No. EP 06851631.9 (7 pgs.).

* cited by examiner

| | PARTICLE SIZE | | |
|---|---|---|---|
| | (FIG. 10) | (FIG. 11) | (FIG. 12) |
| FLOW GAP | 1 μm | 3 μm | 10 μm |
| 3 mm | 38% | 75% | 97% |
| 6 mm | 22% | 33% | 95% |

HAND-HELD TRACE PARTICLE SAMPLING SYSTEM AND METHOD OF OPERATING THE SAME

CROSS REFERENCE TO RELATED APPLICATIONS

This application is a continuation-in-part of U.S. patent application Ser. No. 11/639,579, filed Dec. 15, 2006, entitled, "Hand-held Trace Vapor/Particle Sampling System," which is a divisional U.S. patent application Ser. No. 11/202,455, filed Aug. 11, 2005, now U.S. Pat. No. 7,299,710, which are incorporated by reference herein in their entirety.

BACKGROUND OF THE INVENTION

The embodiments described herein relate generally to a hand-held trace vapor and particle sampling system and, more particularly, to a hand-held trace particle sampling system for enhancing detection of materials of interest.

At least some known hand-held trace particle sampling systems are used to detect trace portions of materials of interest, e.g., residues. As used herein, the term "material of interest" refers to threat compounds and other contraband substances such as explosives, especially home-made explosives (HME), and narcotics that may compose a threat in an inspected region. In addition, such "materials of interest" may include compounds associated with chemical and biological weapons. Such hand-held trace particle sampling systems are portable devices used to detect residue from materials of interest on skin, clothing, parcels, bags, cargo, vehicles, and other surfaces. Therefore, such hand-held trace particle sampling systems are used either as a stand-alone method of detection or are used in conjunction with other systems, e.g., x-ray scanners, metal detectors, and canine patrols, that may use a variety of detection technologies, e.g., mass spectrometry, ion mobility spectrometry, and optical spectroscopy.

Many known hand-held trace particle sampling systems include sample collection, sample concentration, sample delivery, and sample analysis features. However, at least some of such hand-held trace particle sampling systems are not configured to collect and concentrate trace samples sufficiently and may, therefore, experience a non-detect event due to a failure of sufficient sample delivery for analysis.

BRIEF DESCRIPTION OF THE INVENTION

In one aspect, a particle impact device for a hand-held trace particle detection system includes an intake manifold. The intake manifold includes a first conduit defining an intake port that defines a first transport area. The intake manifold also includes a second conduit coupled to the first conduit. The second conduit defines a discharge port that defines a second transport area. The first transport area is greater than the second transport area. The particle impact device also includes a combined deposition and deflection apparatus positioned downstream of the discharge port. The combined deposition and deflection apparatus defines a deposition and deflection surface positioned a predetermined distance from the discharge port. The deposition and deflection surface is configured to deflect a fluid stream and collect at least a portion of particles entrained in the fluid stream.

In another aspect, a method of collecting a trace sample from an object for detection by a detector is provided. The method includes channeling a fluid stream including the trace sample through an intake manifold. The method also includes directing the fluid stream and the trace sample toward a combined deposition and deflection apparatus. The method further includes impinging at least a portion of the trace sample on the combined deposition and deflection apparatus. The method also includes directing the fluid stream around the combined deposition and deflection apparatus.

In yet another aspect, a hand-held trace particle detection system is provided. The hand-held trace particle detection system includes a casing defining a slot and a particle impact device. The particle impact device includes an intake manifold that includes a first conduit defining an intake port that defines a first transport area. The particle impact device also includes a second conduit coupled to the first conduit. The second conduit defines a discharge port that defines a second transport area. The first transport area is greater than the second transport area. The particle impact device also includes a combined deposition and deflection apparatus inserted into the slot and positioned downstream of the discharge port. The combined deposition and deflection apparatus defines a deposition and deflection surface positioned a predetermined distance from the discharge port. The deposition and deflection surface is configured to deflect a fluid stream and collect at least a portion of particles entrained in the fluid stream.

BRIEF DESCRIPTION OF THE DRAWINGS

FIG. 1 is a schematic view of an exemplary hand-held trace particle detection system;

FIG. 2 is a schematic cutaway side view of an exemplary demonstration of the principles of a particle impact device of the hand-held trace particle detection system shown in FIG. 1;

FIG. 3 is a schematic cutaway overhead view of an exemplary particle impact device of the hand-held trace particle detection system shown in FIG. 1;

FIG. 4 is a schematic cutaway side view of the particle impact device shown in FIG. 3;

FIG. 5 is a schematic perspective view of a portion of the particle impact device shown in FIGS. 3 and 4;

FIG. 6 is a schematic side view of the particle impact device shown in FIGS. 3 and 4 with exemplary pressure relationships shown therein;

FIG. 7 is a schematic side view of the particle impact device shown in FIGS. 3 and 4 with exemplary velocity relationships shown therein;

FIG. 8 is a schematic side view of the particle impact device shown in FIGS. 3 and 4 with an exemplary trajectory of particles having a diameter of approximately 3 micrometers (μm);

FIG. 9 is a schematic side view of the particle impact device shown in FIGS. 3 and 4 with an exemplary trajectory of particles having a diameter of approximately 10 micrometers (μm);

FIG. 10 is a schematic view of an exemplary distribution of particles having a diameter of approximately 1 micrometer (μm) using the particle impact device shown in FIGS. 3, 4, and 6-9;

FIG. 11 is a schematic view of an exemplary distribution of particles having a diameter of approximately 3 micrometers (μm) using the particle impact device shown in FIGS. 3, 4, and 6-9;

FIG. 12 is a schematic view of an exemplary distribution of particles having a diameter of approximately 10 micrometers (μm) using the particle impact device shown in FIGS. 3, 4, and 6-9;

FIG. 13 is a tabular view of the distributions shown in FIGS. 10, 11, and 12;

FIG. 14 is a schematic cutaway side view of an exemplary alternative particle impact device that may be used with the hand-held trace particle detection system shown in FIG. 1; and FIG. 15 is a schematic cutaway side view of an exemplary alternative particle impact device that may be used with the hand-held trace particle detection system shown in FIG. 1.

DETAILED DESCRIPTION OF THE INVENTION

The hand-held trace particle detection systems described herein provide a cost-effective method for detecting trace portions of materials of interest, e.g., residues. Specifically, the hand-held trace particle detection systems described herein are configured to collect and concentrate trace samples sufficiently to obtain a sufficient sample for delivery to the analysis equipment, thereby significantly reducing non-detect events. More specifically, the embodiments described herein include a particle impact device that includes an intake manifold that facilitates a pressure profile and a velocity profile that facilitates collection of the sample from the surface of an object. Also, the embodiments described herein include a combined deposition and deflection apparatus positioned downstream of that defines a deposition and deflection surface configured to deflect a fluid stream and collect at least a portion of particles entrained in the fluid stream. The embodiments of the deposition and deflection surface may include a dosimeter film or sensor configured to capture the particles or a porous material configured to be heated and to at least partially vaporize the particles. Other active collection surfaces may also be used. The deflected fluid stream is channeled away from the collected particles through a fluid deflection channel. In addition, the hand-held trace particle detection systems described herein include an air jet impingement manifold extending about the intake manifold and directs a jet of fluid onto an object to facilitate sample dislodgement.

Figure 1:
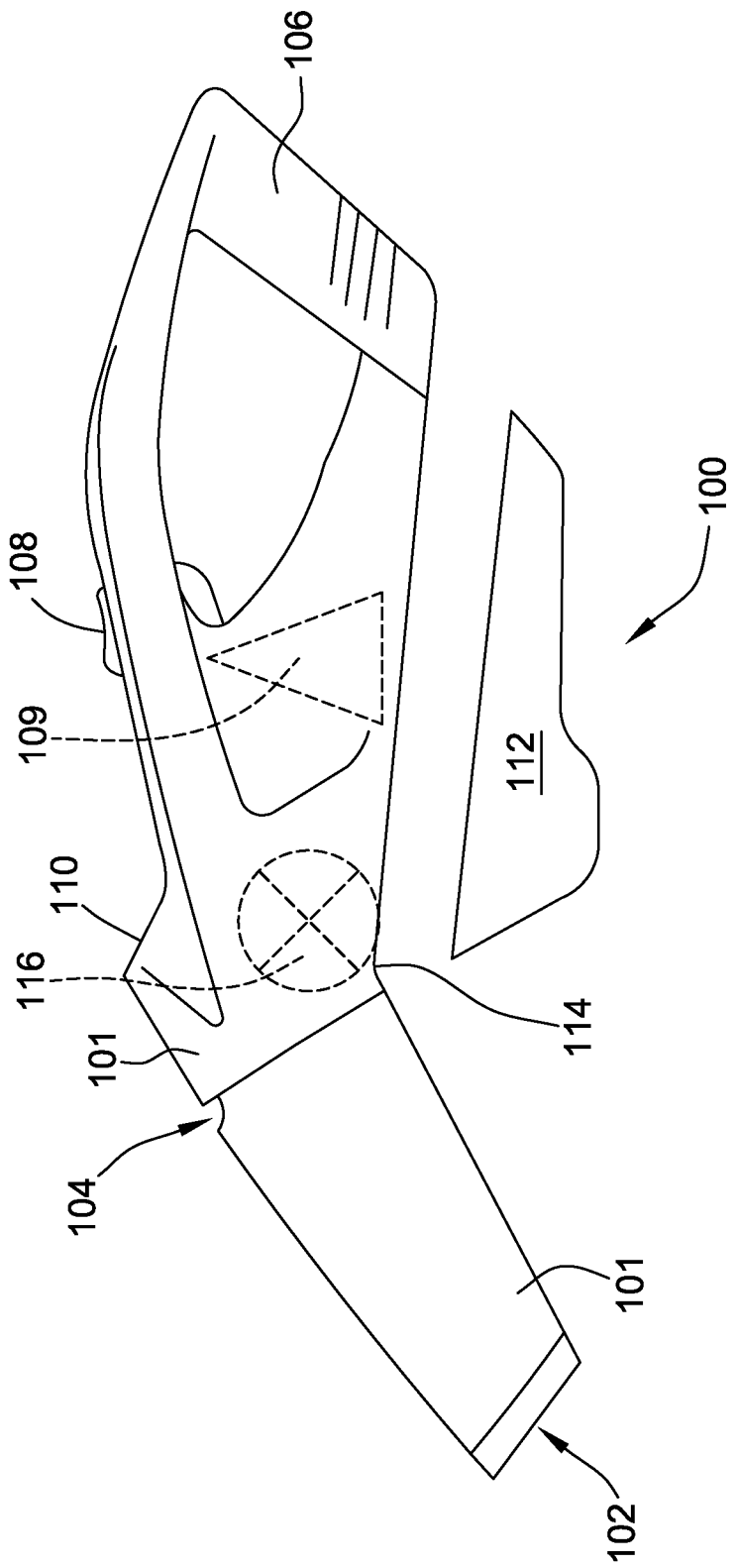
FIGS. 1-15 show exemplary embodiments of the systems and methods described herein.

FIG. 1 is a schematic view of an exemplary hand-held trace particle detection system 100. In the exemplary embodiment, hand-held trace particle detection system 100 includes a housing or casing 101. Casing 101 at least partially defines an intake port 102. A sample cartridge slot 104 is defined in casing 101 and is configured to receive a sample cartridge (not shown ion FIG. 1). In the exemplary embodiment, electric power is provided by a battery 106 and controlled through a trigger device 108 that includes, without exception, a slidable ON/OFF switch or a depressible button. Electric power may also be supplied from a standard 110-volt outlet. Hand-held trace particle detection system 100 is controlled by a programmable controller 109 and monitored through an interface 110, including, without exception, a liquid crystal display monitor, a touch screen, and a keypad. The number of collected samples can be displayed by monitor 110. A detector 112 is mounted on a bottom 114 of system 100. Alternatively, detector 112 may be mounted to any portion of system 100 that enables operation of detector 112 and system 100 as described herein, including, without limitation, internal to casing 101. System 100 also includes a fluid transport apparatus 116 that is any device that moves a fluid, e.g., air that enables operation of system 100 as described here, for example, and without exception, a fan, a pump, and a blower. System 100 includes any number of fluid transport apparatus 116 that enables operation of system 100 as described here.

In operation, a first mode of operation includes sliding trigger device 108 from OFF to ON to energize fluid transport apparatus 116 continuously until trigger 108 is released. A jet of air (not shown in FIG. 1) is directed from fluid transport apparatus 116 through intake port 102 toward a surface of an object (neither shown in FIG. 1). Also, a suction induced by fluid transport apparatus 116 pulls particle samples (not shown in FIG. 1) into casing 101 for transfer to a sample cartridge (not shown in FIG. 1) for analysis by detector 112. Controller 109 regulates operation of fluid transport apparatus 116 and detector 112. Alternatively, programmed operation may be used, such programmed operation including, for example, one or more samplings with a predetermined, fixed-duration sampling period initiated through depression of trigger device 108. Multiple depressions of trigger device 108 may be used to activate fluid transport apparatus 116 for the fixed-duration sampling period multiple times for a single object to cover the desired areas thereof.

Figure 2:
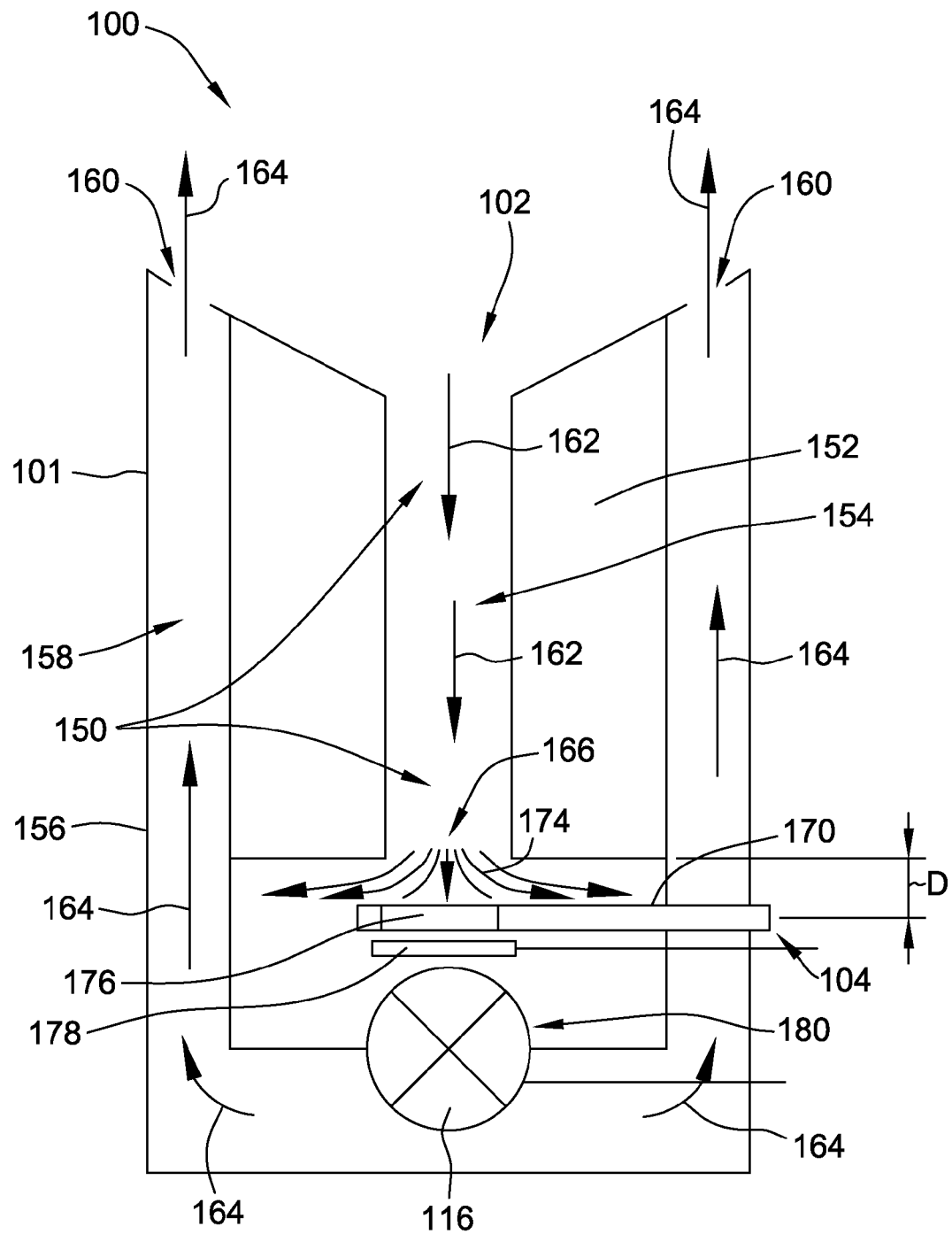

FIG. 2 is a schematic cutaway side view of an exemplary demonstration of the principles of a particle impact device 150 of hand-held trace particle detection system 100. Particle impact device 150 includes an intake manifold 152 that defines air intake port 102 and a sample transport channel 154. Casing 101 and intake manifold 152 define an air jet impingement manifold 156 that defines an air jet impingement channel 158 and an air jet impingement port 160. Air jet impingement port 160 and air intake port 102 are proximate each other and define a substantially annular configuration. Fluid transport apparatus 116 is coupled in flow communication with air intake port 102 and sample transport channel 154. Fluid transport apparatus 116 is also coupled in flow communication with air jet impingement channel 158 and air jet impingement port 160. When energized, fluid transport apparatus 116 induces a suction flow as indicated by arrows 162. Also, when energized, fluid transport apparatus 116 induces an air jet impingement flow, as indicated by arrows 164, thereby directing a jet of fluid onto an object (not shown) through air jet impingement manifold 156. Sample transport channel 154 defines a discharge port 166.

Also, particle impact device 150 includes a combined deposition and deflection apparatus 170 positioned downstream of discharge port 166. Combined deposition and deflection apparatus 170 defines a deposition and deflection surface 172 positioned a predetermined distance D from discharge port 166. Deposition and deflection surface 172 is configured to deflect a fluid stream (defined by arrows 174) and collect at least a portion of particles (not shown in FIG. 2) entrained in fluid stream 174. In this embodiment, combined deposition and deflection apparatus 170 is a sample cartridge inserted into sample cartridge slot 104. The sample cartridge includes a dosimeter sensor 176 and a transceiver 178. Sensor 176 of combined deposition and deflection apparatus 170 is mounted on a replaceable cartridge that does not impede the air-jet impinger or the intake flow. Transceiver 178 is fixedly mounted. Combined deposition and deflection apparatus 170 and casing 101 at least partially define a fluid deflection channel 180 coupled in flow communication with fluid transport apparatus 116.

Combined deposition and deflection apparatus 170 acts as a momentum impactor that facilitates impingement of the particles on the sensor surface, i.e., deposition and deflection surface 172, while deflecting the air flow. Variables that have predetermined ranges to facilitate particle collection in a particle diameter range between approximately 3 microns (μm) and approximately 30 μm include, without limitation, the volumetric flow rate through sample transport channel 154, the inner diameter of fluid deflection channel 180, which governs the linear flow velocity, and the annular height and area transverse to deposition and deflection surface 172 to match the conductance of sample transport channel 154 and the major transverse flows, i.e., suction flow 162 and fluid stream 174. Fluid stream 174 is channeled to the pressure side of fluid transport apparatus 116 and delivered through air jet impingement port 160 onto the sampling surface (not shown in FIG. 2). Alternative embodiments of combined deposition and deflection apparatus 170 include, without limitation, any chemical analysis device that enables operation of particle detection system 100, including, without limitation, a heated porous metal surface that vaporizes the particles so that the vapors enter into a detector device for analysis. Such metal surface may be always hot to give immediate vaporization or it could be turned on and off at designated times, e.g., with trigger device 108.

Figure 3:
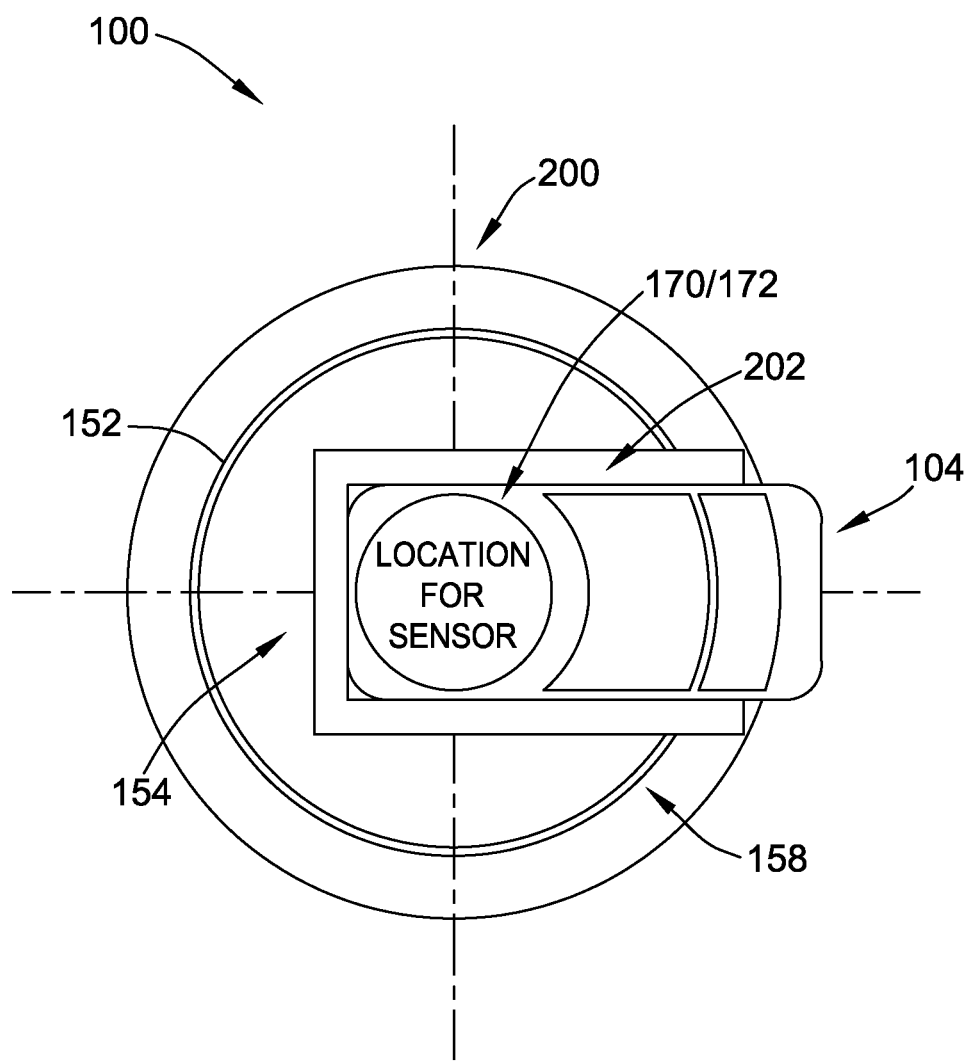

FIG. 3 is a schematic cutaway overhead view of an exemplary particle impact device 200 that may be used with hand-held trace particle detection system 100. Particle impact device 200 is similar to particle impact device 150 (shown in FIG. 2) with the exception of device 200 having a guide 202 extending through air jet impingement channel 158 and partially into intake manifold 152. Guide 202 is coincident with sample cartridge slot 104. Guide 202 facilitates insertion and removal of combined deposition and deflection apparatus 170.

Figure 4:
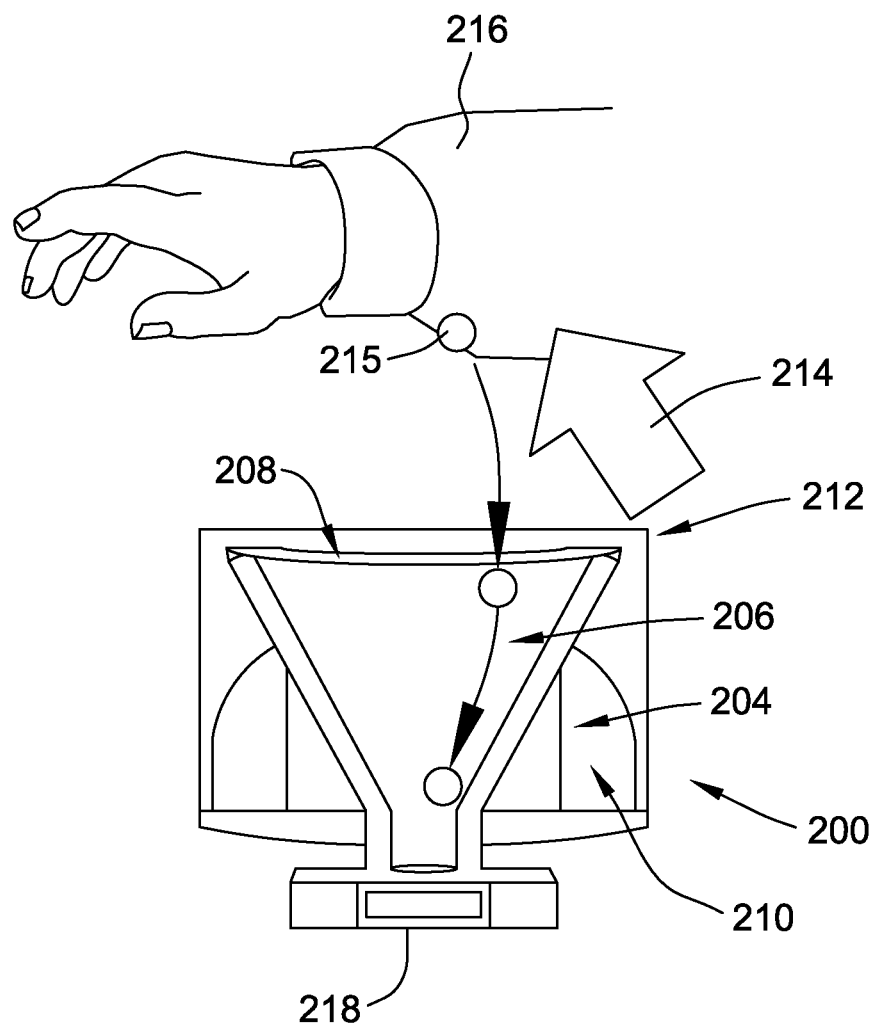

FIG. 4 is a schematic cutaway side view of particle impact device 200. Particle impact device 200 includes an intake manifold 204 that defines a sample transport channel 206 and a wide-mouthed air intake port 208. A portion of intake manifold 204 and sample transport channel 206 are frustoconical. The frustoconical configuration facilitates velocity and pressure profiles within sample transport channel 206 as described below. Particle impact device 200 also includes an air jet impingement channel 210 that narrows from fluid transport apparatus 116 (shown in FIGS. 1 and 2) to an air jet impingement port 212 such that a pressure with channel 210 and velocity of impingement air jets 214 exiting port 212 are increased to facilitate dislodging particles 215 (only one shown in FIG. 4) from an object 216. Particles 215 are directed toward a sensor 218.

Figure 5:
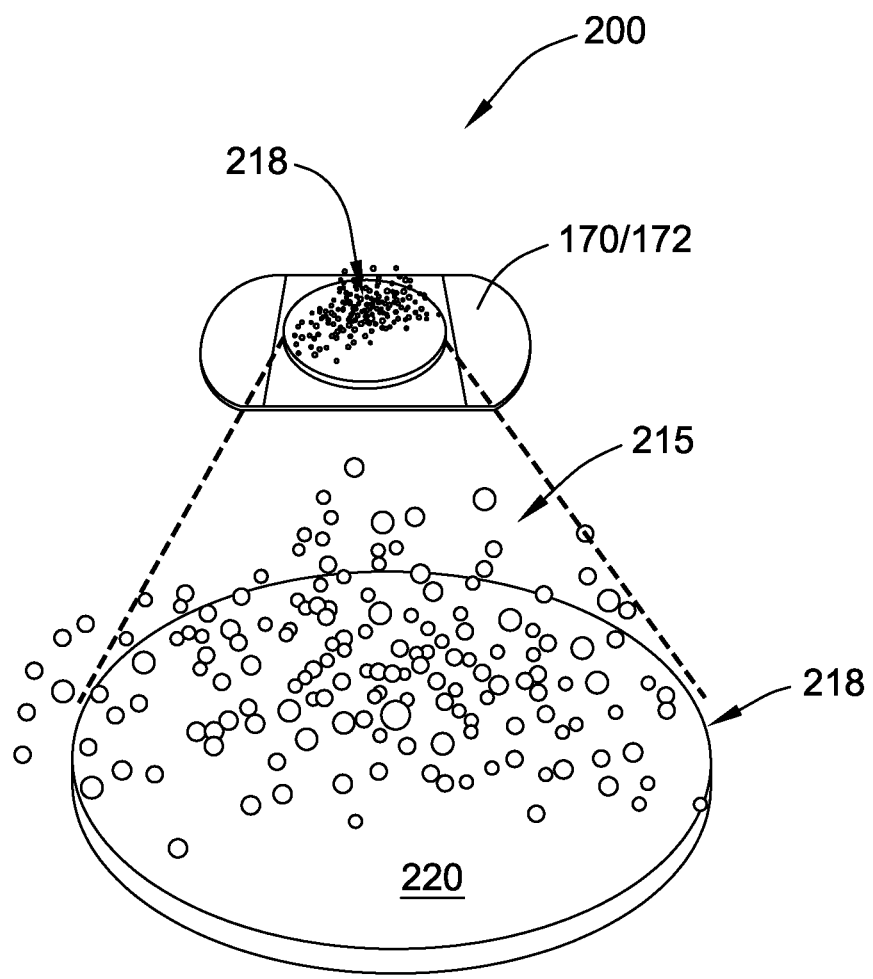

FIG. 5 is a schematic perspective view of a portion of particle impact device 200, i.e., combined deposition and deflection apparatus 170 and deposition and deflection surface 172 as defined by sensor 218. Sensor 218 includes a sensor surface 220 that at least partially defines surface 172. Predetermined values of air flow across sensor surface 220 facilitates capture of particles 215 by sensor 218.

Figure 6:
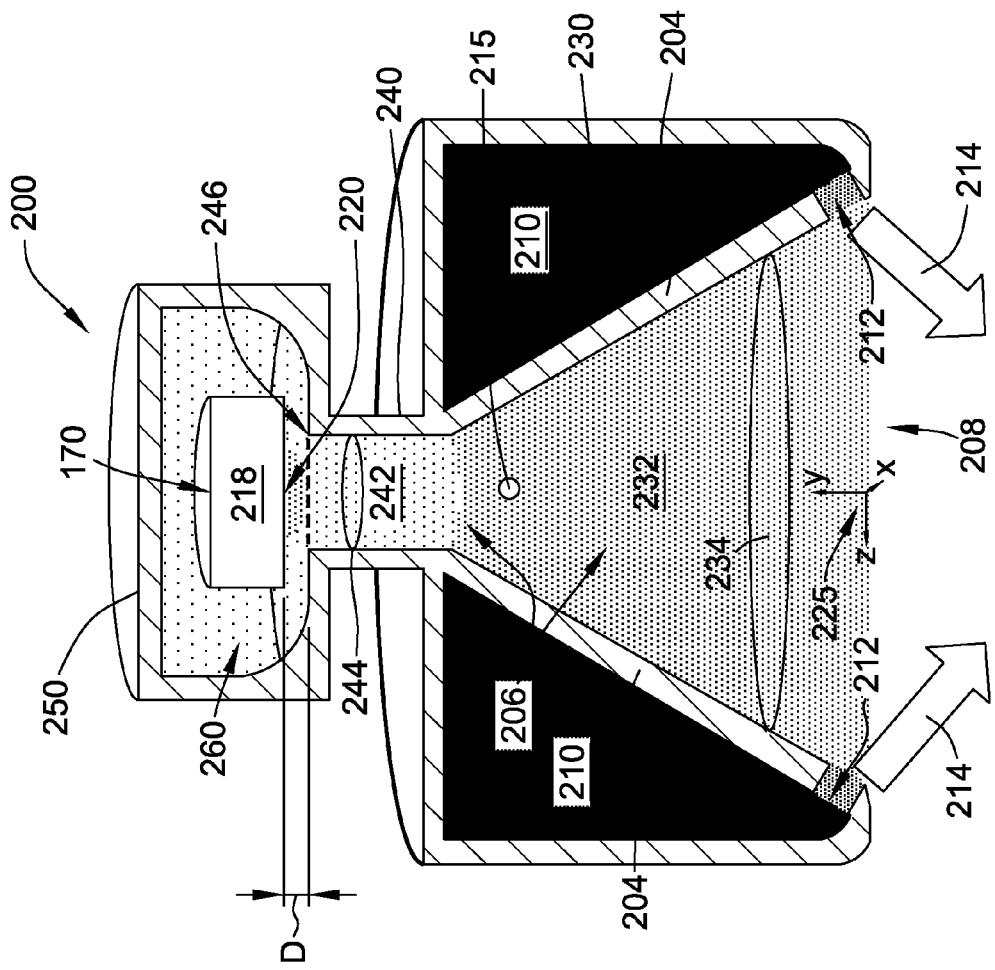

FIG. 6 is a schematic side view of particle impact device 200 with exemplary pressure relationships shown therein. A set of orthogonal axes 225, i.e., a horizontal z-axis, a vertical y-axis, and an x-axis (shown perpendicular to page) are shown for reference. In the exemplary embodiment, particle impact device 200 includes intake manifold 204 and sample transport channel 206. Intake manifold 204 includes a frustoconical first conduit 230 that defines a frustoconical first portion 232 of sample transport channel 206. Frustoconical first conduit 230 also defines wide-mouthed air intake port 208 that is substantially circular and parallel to the z-axis. First conduit 230 further defines a first transport area 234 parallel to air intake port 208 that varies as a function of position along the y-axis.

Intake manifold 204 also includes a cylindrical second conduit 240 coupled to first conduit 230. Cylindrical second conduit 240 defines a cylindrical second portion 242 of sample transport channel 206 that is coupled in flow communication with first portion 232. Second conduit 240 also defines a second transport area 244 parallel to air intake port 208 that is substantially constant as a function of position along the y-axis. Second transport area 244 is less than first transport area 234. Second conduit 240 further defines a discharge port 246 positioned a predetermined distance D from sensor 218 of combined deposition and deflection apparatus 170. Discharge port 246 and surface 172 (shown in FIG. 5) of sensor 218 are substantially parallel.

Also, in the exemplary embodiment, particle impact device 200 includes a housing 250 extending about combined deposition and deflection apparatus 170 such that a fluid deflection channel 260 is at least partially defined around apparatus 170. Fluid deflection channel 260 is coupled in flow communication with fluid transport apparatus 116 (shown in FIGS. 1 and 2).

Further, in the exemplary embodiment, pressure relationships with defined parameters are shown. The pressure relations shown are based on air intake port being approximately 5 millimeters (mm) (0.2 inches (in.)) from the surface of object 216 (shown in FIG. 4), though the effect would be similar for larger distances. In operation, with fluid transport apparatus 116 in operation, air jet impingement channel 210 operates in a pressure range between approximately 101,651 Pascal (Pa) (14.74 pounds per square inch absolute (psia)) and approximately 102,025 Pa (14.80 psia). Since one standard atmosphere is approximately equivalent to 101,325 Pa (14.7 psia), air jet impingement channel 210 operates slightly above atmospheric pressure to form impingement air jets 214.

Also, in operation, first portion 232 of sample transport channel 206 operates in a pressure range between approximately 100,965 Pa (14.64 psia) and approximately 101,141 Pa (14.74 psia). Second portion 242 of sample transport channel 206 operates in a pressure range between approximately 100,612 Pa (14.59 psia) and approximately 100,965 Pa (14.64 psia). Therefore, a negative pressure gradient is induced within sample transport channel 206. Further, in operation, fluid deflection channel 260 operates in a pressure range between approximately 100,082 Pa (14.52 psia) and approximately 100,612 Pa (14.59 psia).

The pressures and pressure ranges described above are exemplary and any pressures and pressure ranges that enable operation of particle impact device 200 and hand-held trace particle detection system 100 as described herein may be used.

Figure 7:
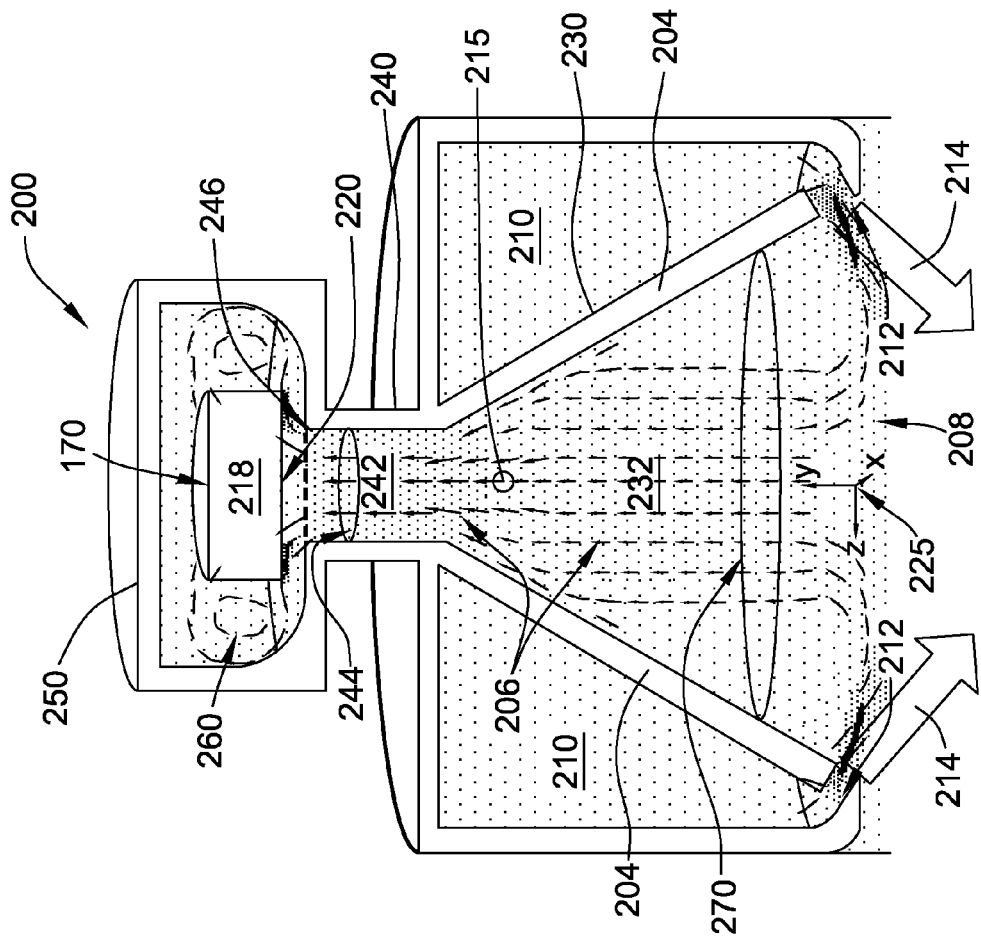
Figure 7:
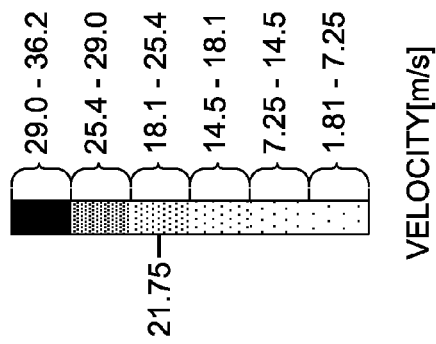

FIG. 7 is a schematic side view of particle impact device 200 with exemplary velocity relationships shown therein. In operation, with fluid transport apparatus 116 in operation, air in air jet impingement channel 210 has a velocity in a range between approximately 1.81 meters per second (m/s) (6.27 inches per second (in./s)) and approximately 21.75 m/s (71.4 in./s) such that the velocity of air increases as it approaches air jet impingement ports 212. The air in impingement air jets 214 has a velocity in a range between approximately 21.75 m/s (71.4 in./s) and 36.3 m/s (118.9 in./s).

Also, in the exemplary embodiment, the air velocities in sample transport channel 206 defines an increasing velocity gradient to transport particles 215 therethrough. First portion 232 of sample transport channel 206 defines a velocity profile 270 that includes lower velocities in a range between approximately 1.81 (m/s) (6.27 in./s) and 7.25 m/s (23.8 in./s) in the regions closest to first conduit 230. Velocity profile 270 also includes higher velocities in a range between approximately 7.25 m/s (23.8 in./s) and approximately 14.5 m/s (45.6 in./s) in the center region of channel 206. The air velocity increases to approximately 18.1 m/s (59.5 in./s) as it approaches second portion 242 of channel 206.

Further, in the exemplary embodiment, second portion 242 of channel 206 defines a velocity profile 272 that includes accelerated air flow velocities of in a range between approximately 18.1 m/s (59.5 in./s) and approximately 25.4 m/s (83.3 in./s). As the air impinges sensor 218 and is diverted into fluid deflection channel 260, the air velocity decreases to a range between approximately 1.81 (m/s) (6.27 in./s) and approximately 18.1 m/s (59.5 in./s) after a slight acceleration to velocities in a range between approximately 29.0 m/s (95.2 in./s) and approximately 36.2 m/s (118.9 in./s) in the regions between sensor 218 and housing 250 having distance D therebetween.

The velocities and velocity ranges described above are exemplary and any velocities and velocity ranges that enable operation of particle impact device 200 and hand-held trace particle detection system 100 as described herein may be used.

Figure 8:
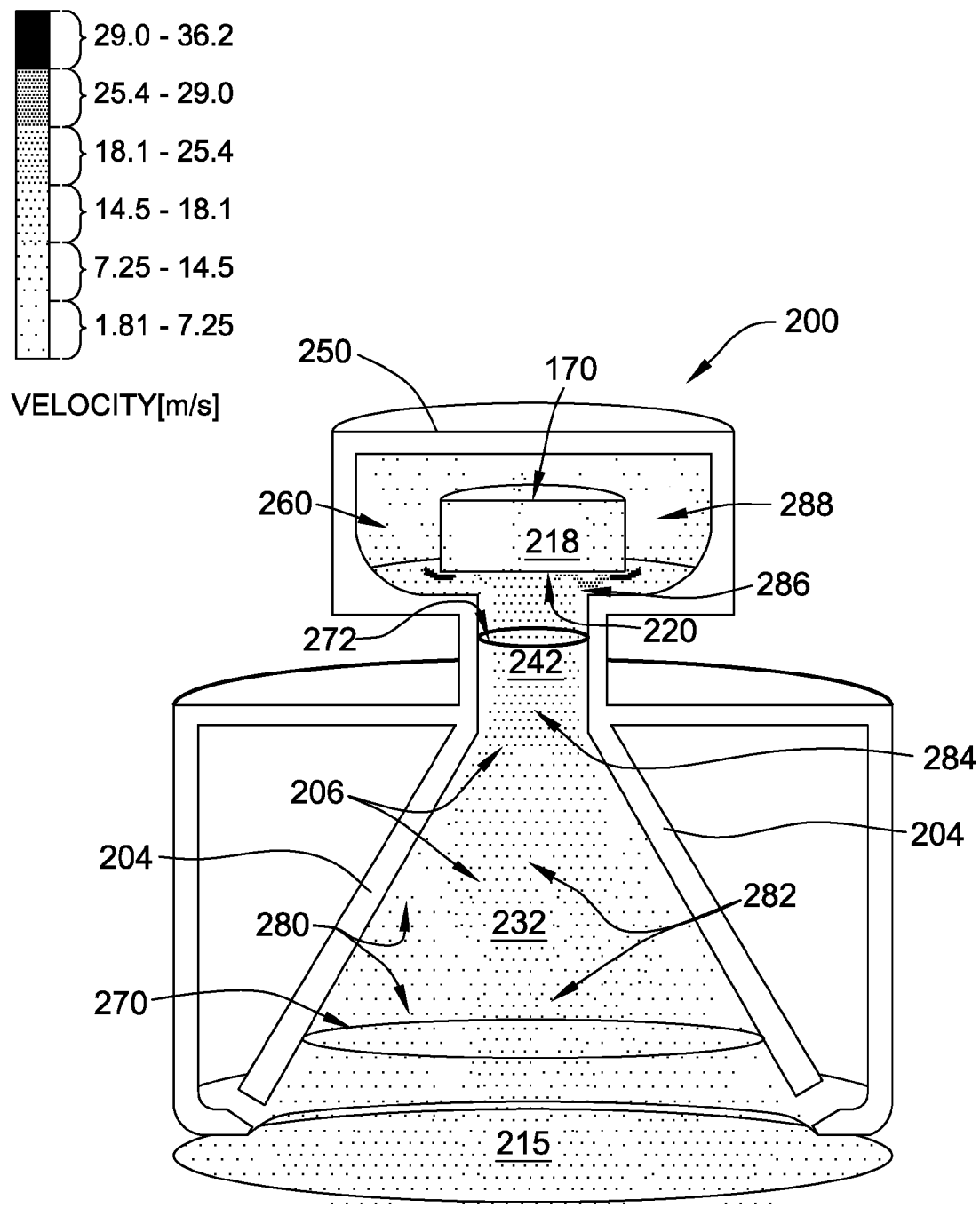

FIG. 8 is a schematic side view of particle impact device 200 with an exemplary trajectory 300 of particles 215 having a diameter of approximately 3 micrometers (μm). In the exemplary embodiment, the particle velocities in particle impact device 200 are similar to the air velocities shown in FIG. 7 with the exception that the velocities of particles in the center of first portion 232 have a broader range between approximately 3.63 m/s (12.6 in./s) and approximately 14.5 m/s (45.6 in./s). The trajectories of particles 215 are such that the trajectory profile approximates that of the velocities. There is a concentration of lower velocity particles 280 in the regions closest to first conduit 230. There is a slightly higher concentration of higher velocity particles 282 in the center region of channel 206. A concentration of high velocity particles 284 increases as they approach and enter second portion 242 of channel 206. A significant portion of particles 286 are captured by sensor 218 and a remainder of particles 288 are channeled into fluid deflection channel 260.

In general, the 3 μm particles 215 have a relatively flat density gradient in first portion 232 with a slight increase in population density towards the center of first portion 232.

Figure 9:
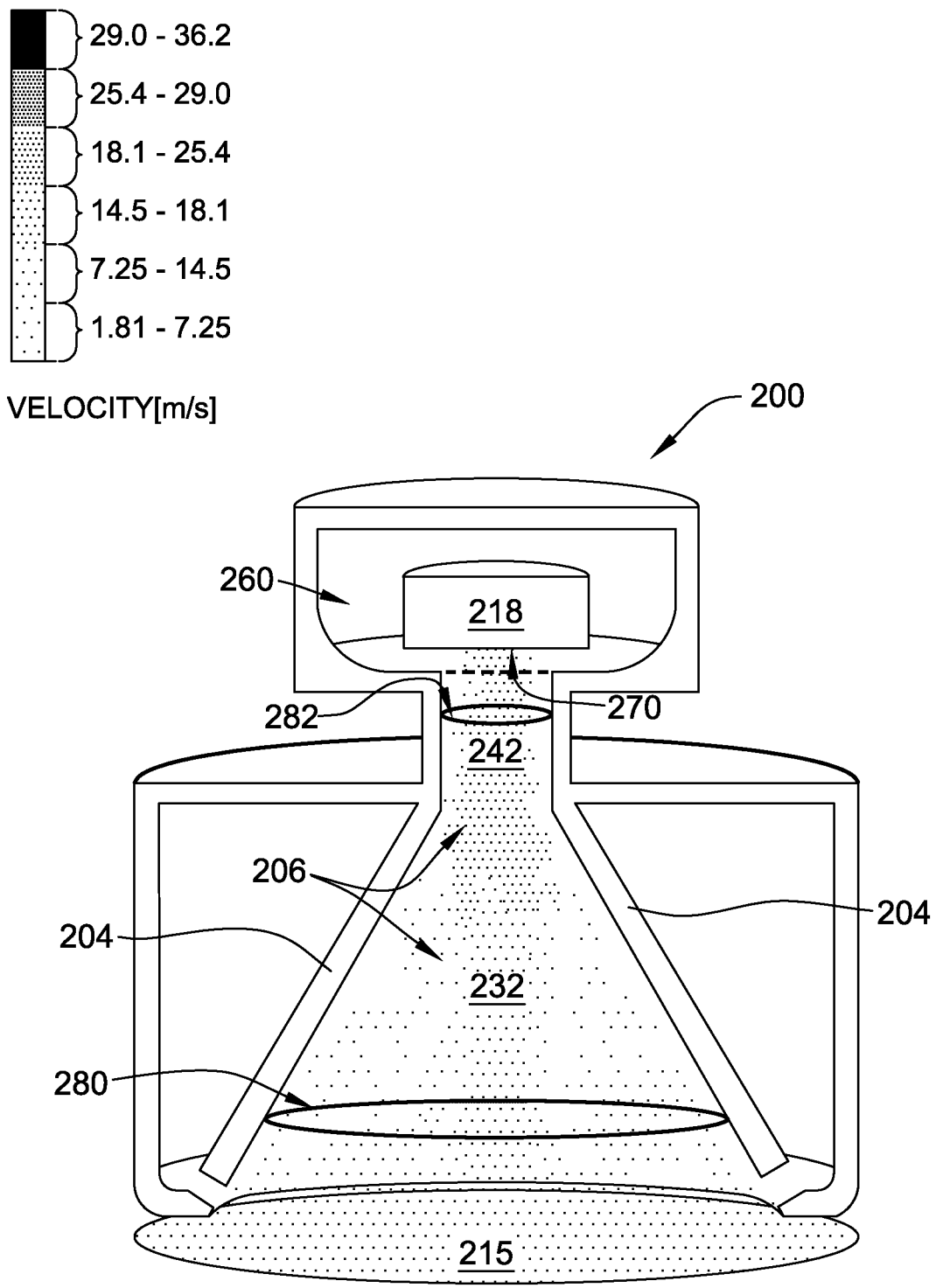
Figure 10:
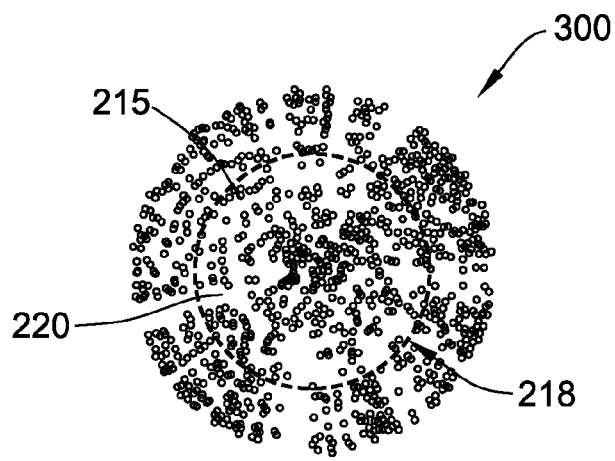
Figure 11:
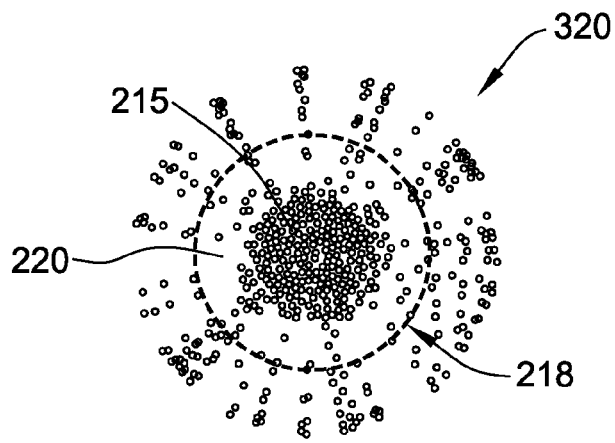
Figure 12:
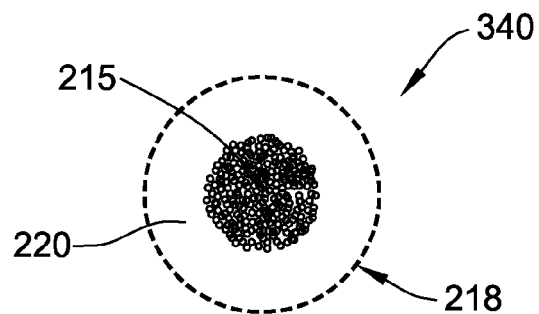
Figure 13:

FIG. 9 is a schematic side view of particle impact device 200 with an exemplary trajectory of particles 215 having a diameter of approximately 10 micrometers (μm). The particle velocities for the 10 μm particles 215 are more uniform in first portion 232 and are higher toward the center of first portion 232 for the 10 μm particles 215 as compared to the 3 μm particles 215 (shown in FIG. 8). Velocity profile 280 includes higher velocities toward the center of first portion 232 in a range between approximately 7.25 m/s (23.8 in./s) and approximately 14.5 m/s (45.6 in./s). In general, the 10 μm particles 215 have a relatively low density in the regions closest to first conduit 230 and a relatively high density toward the center of first portion 232 with a steep gradient therebetween.

Figure 14:
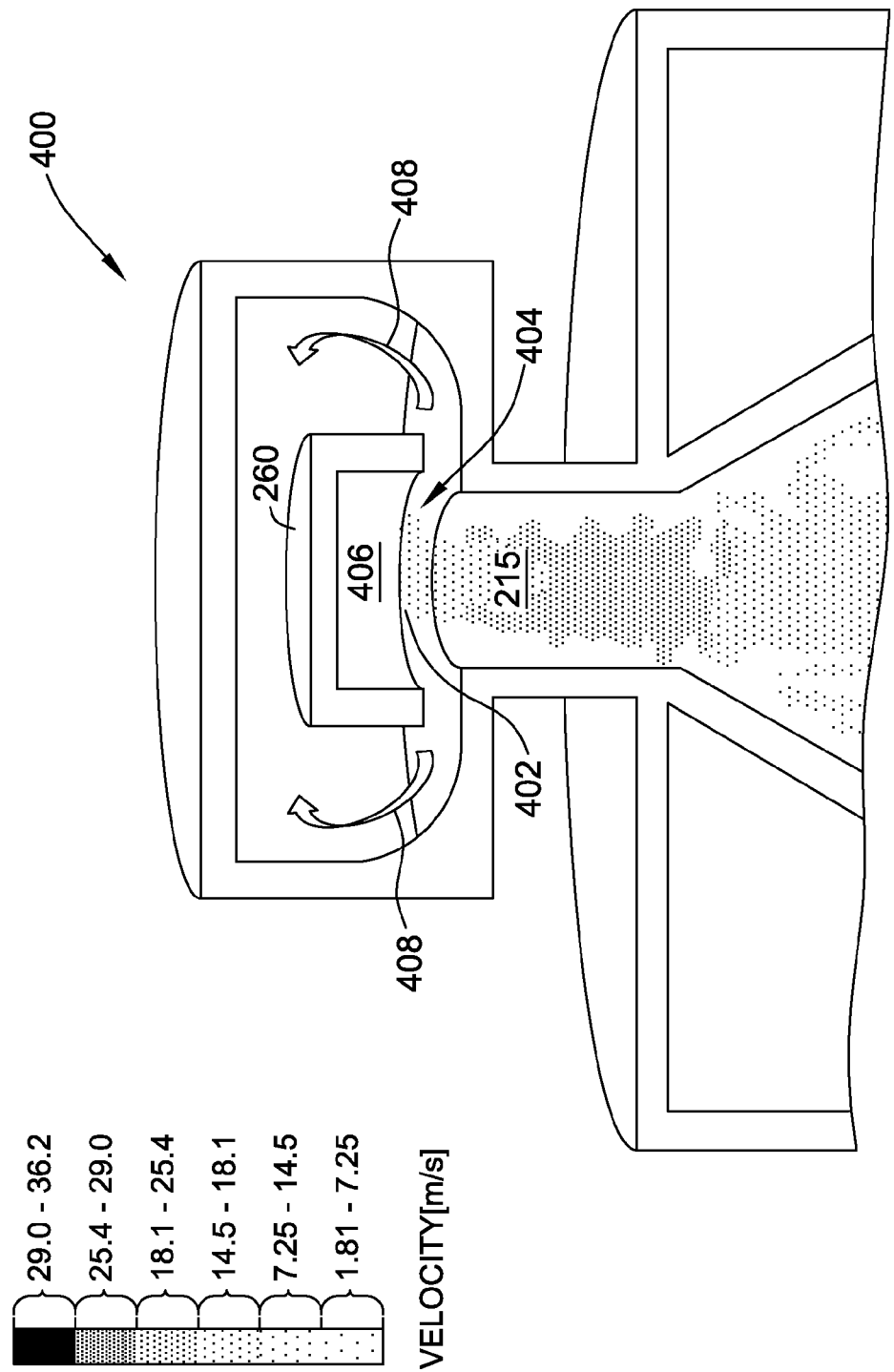
Figure 15:
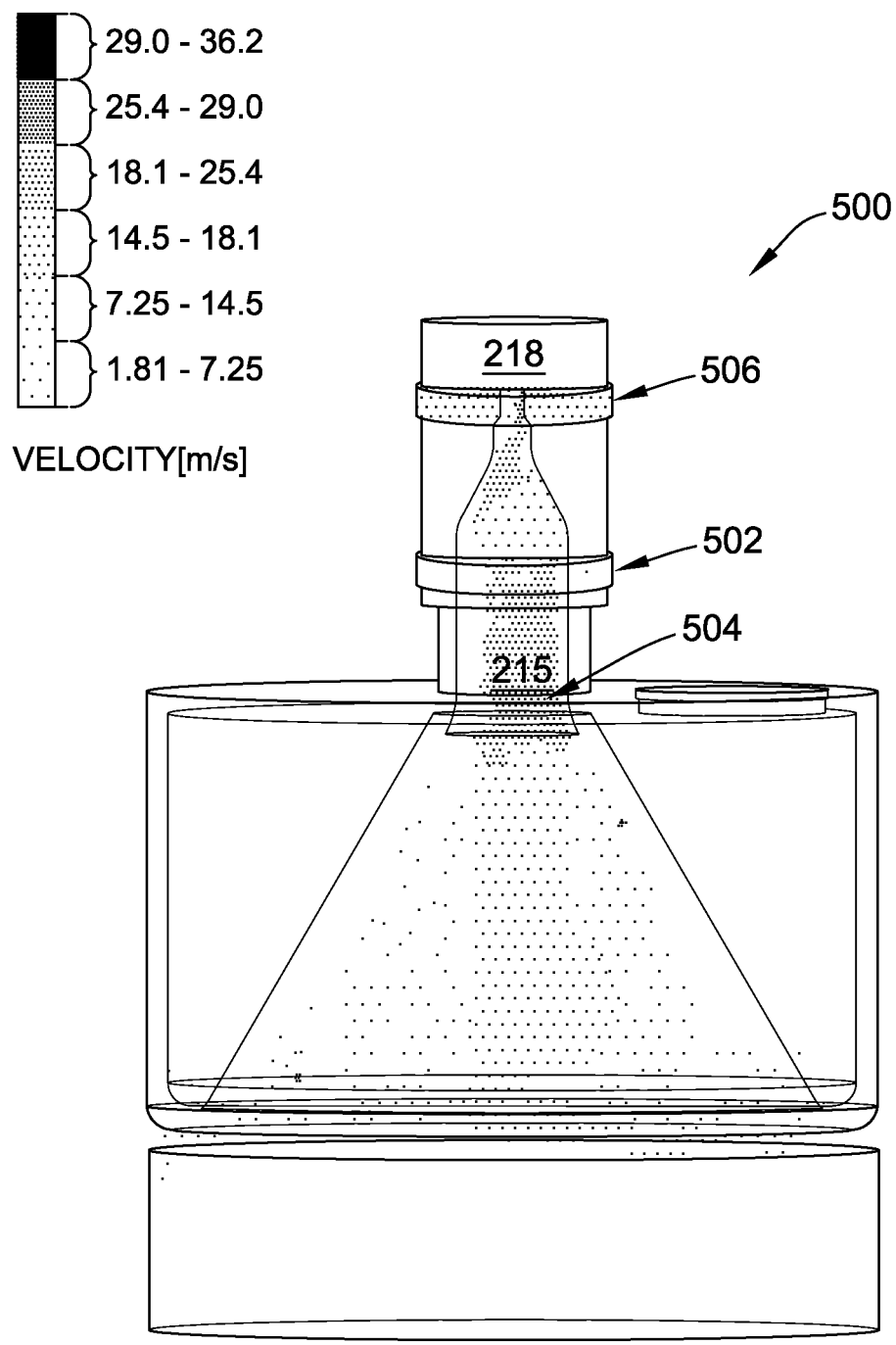

Also, second portion 242 defines a velocity profile 282 that includes accelerated air flow velocities of in a range between approximately 18.1 m/s (59.5 in./s) and approximately 25.4 m/s (83.3 in./s) until the approach to sensor 218. There, the particles decelerate to a velocity range between approximately 14.5 m/s (47.6 in./s) and 18.1 m/s (59.5 in./s). As particles 215 impinge sensor 218, most are collected and few are diverted into fluid deflection channel 260.

In the exemplary embodiment, particle impact device 200 is enabled to operate with particles in the range between 3 μm and 30 μm, which corresponds to the peak in the mass-weighted particle size distribution for explosives contamination on people and with varying flow conditions.

FIG. 10 is a schematic view of an exemplary distribution 300 of particles 215 having a diameter of approximately 1 μm using particle impact device 200 (shown in FIGS. 3, 4, and 6-9). FIG. 11 is a schematic view of an exemplary distribution 320 of particles 215 having a diameter of approximately 3 μm using particle impact device 200. FIG. 12 is a schematic view of an exemplary distribution 340 of particles 215 having a diameter of approximately 10 μm using particle impact device 200.

The trajectories of particles 215 of different sizes striking sensor 218 having a diameter of approximately 25 mm (1.0 in.) are shown in FIGS. 10, 11, and 12. FIG. 10 shows that 1 μm particles with varying velocities have a strike probability of approximately 38%. FIG. 11 shows that 3 μm particles with varying velocities have a strike probability of approximately 75%. FIG. 12 shows that 10 μm particles with varying velocities have a strike probability of approximately 97%. Therefore, a qualitative indication of the impact efficiency for particles of different size collected off a person onto sensor 218 for particle sizes 1, 3, and 10 μm are 38%, 75%, and 97%, respectively. By extrapolation, 30 μm particles are determined to be deposited onto sensor 218 with greater than 97% efficiency.

FIG. 13 is a tabular view, i.e., table 360 of distributions 300, 320, and 340 shown in FIGS. 10, 11, and 12, respectively for transverse flow gaps with measurement D (shown in FIGS. 2 and 6) of 3 mm (0.12 in.) and. 6 mm (0.24 in.). The impact probabilities decrease significantly for 1 μm and 3 μm particles while the impact probabilities are nearly 100% for both cases for the 30 μm particles. Therefore, for particles in a range between approximately 3 μm and 30 μm, and with a properly sized transverse flow gap measurement D, particle impact device 200 demonstrates a high probability of success for transferring explosives particles from the surface of people to the sensor surface.

Regarding sampling time, longer collection times facilitate more complete particle removal from the person and/or object and also the capability to cover a larger surface area from the person and/or object. The actual collection of particles onto the sensor once the particle is removed from the person and/or object is nearly instantaneous.

FIG. 14 is a schematic cutaway side view of an exemplary alternative particle impact device 400 that may be used with hand-held trace particle detection system 100 (shown in FIG. 1). In this alternative exemplary embodiment, an alternative deposition and deflection surface 402 is recessed to define a fluid stagnation zone 404 within an alternative sensor 406. Stagnation zone 404 significantly decreases air flow across surface 402 of sensor 406. A significant portion of air flow 408 is diverted away from the surface 402 and the momentum of particles 215 carries them to sensor surface 402. This method also facilitates particles 215 to decelerate prior to hitting sensor surface 402, thereby facilitating increased deposition efficiency without re-bouncing of particles 215.

FIG. 15 is a schematic cutaway side view of an exemplary alternative particle impact device 500 that may be used with hand-held trace particle detection system 100 (shown in FIG. 1). In this alternative exemplary embodiment, particle impact device 500 is a multi-stage impactor where a first stage 502 diverts approximately 90% of flow 504 and a second stage 506 diverts approximately 10% of flow in order to reduce the air flow across the surface of sensor 218. Particle impact device 500 facilitates particle transfer efficiency to sensor 218 and also facilitates use of a smaller sensor area if that is deemed desirable. Particle impact device 500 is shown as a two-stage impactor. However, any number of stages that enables operation of particle impact device 500 as described herein may be used. Also, in the exemplary embodiment, a 90%-10% ratio between first stage 502 and second stage 506 are described. However, any ratio of air flow reduction distributed between any number of stages that enables operation of particle impact device 500 and hand-held trace particle detection system 100 as described herein may be used.

Referring to FIGS. 14 and 15 together, particle impact device 500 may be used with recessed deposition and deflection surface 402 to define fluid stagnation zone 404. Particle impact device 500 and recessed sensor stagnation zone 404 facilitate slowing down particles 215 impacting the surface film (not shown) of sensor 218.

The depth of sensor stagnation zone 404 in the impact zone may be varied, thereby varying the impact frequency of particles 215 on sensor 406. A two-stage impactor such as impact device 400 also facilitates diverting the majority, i.e., greater than approximately 90% of primary flow 408 away from sensor 406 and allowing only the particle enriched secondary flow to impact sensor surface 402. A combination of two-stage impaction and stagnation zone should achieve the range of flow rates across surface 402 that sensor 406 can tolerate.

The above described hand-held trace particle detection systems provide a cost-effective method for detecting trace portions of materials of interest, e.g., residues. Specifically, the hand-held trace particle detection systems described herein are configured to collect and concentrate trace samples sufficiently to obtain a sufficient sample for delivery to the analysis equipment, thereby significantly reducing non-detect events. More specifically, the embodiments described herein include a particle impact device that includes an intake manifold that facilitates a pressure profile and a velocity profile that facilitates collection of the sample from the surface of an object. Also, the embodiments described herein include a combined deposition and deflection apparatus positioned downstream of that defines a deposition and deflection surface configured to deflect a fluid stream and collect at least a portion of particles entrained in the fluid stream. The embodiments of the deposition and deflection surface may include a dosimeter film or sensor configured to capture the particles or a porous material configured to be heated and to at least partially vaporize the particles. Other active collection surfaces may also be used. The deflected fluid stream is channeled away from the collected particles through a fluid deflection channel. In addition, the hand-held trace particle detection systems described herein include an air jet impingement manifold extending about the intake manifold and directs a jet of fluid onto an object to facilitate sample dislodgement.

A technical effect of the systems and methods described herein includes at least one of: (a) more effective collection of sample particles using a hand-held device; and (b) more effective and accurate analysis and detection of materials of interest due to the increased sample size.

Exemplary embodiments of hand-held trace particle detection systems and methods of using the same are described above in detail. The methods and systems are not limited to the specific embodiments described herein, but rather, components of systems and/or steps of the methods may be utilized independently and separately from other components and/or steps described herein. For example, the methods may also be used in combination with other detection systems and methods, and are not limited to practice with only the detection systems and methods as described herein. Rather, the exemplary embodiment may be implemented and utilized in connection with many other trace particle detection system applications, including, without limitation, non-handheld devices such as a desktop analyzer or as a part of a larger screening system.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A particle impact device for a hand-held trace particle detection system, said particle impact device comprising:
    a first conduit defining an intake port defining a first transport area, said first conduit at least partially defining an air jet impingement port proximate said intake port, said air jet impingement port and said intake port defining a substantially annular configuration; and
    a second conduit coupled to said first conduit, said second conduit defining a discharge port defining a second transport area, said first transport area greater than said second transport area; and
    a combined deposition and deflection apparatus positioned downstream of said discharge port, said combined deposition and deflection apparatus defines a deposition and deflection surface positioned a predetermined distance from said discharge port, said deposition and deflection surface configured to deflect a fluid stream and collect at least a portion of particles entrained in the fluid stream.

2. The particle impact device in accordance with claim 1, wherein said first conduit is frustoconical and said second conduit is cylindrical.

3. The particle impact device in accordance with claim 1, wherein at least a portion of said deposition and deflection surface comprises at least one of:
    a dosimeter film configured to capture the at least a portion of the particles; and
    a porous material configured to be heated and at least partially vaporize the at least a portion of the particles.

4. The particle impact device in accordance with claim 1 further comprising a fluid transport apparatus configured to induce a negative pressure gradient within said first conduit and said second conduit.

5. The particle impact device in accordance with claim 1, wherein said first conduit and said second conduit are configured to induce an increasing velocity gradient within said first conduit and said second conduit.

6. The particle impact device in accordance with claim 1, wherein said deposition and deflection surface is substantially parallel to said discharge port.

7. The particle impact device in accordance with claim 1 further comprising a housing extending about said combined deposition and deflection apparatus, wherein said combined deposition and deflection apparatus and said housing define a fluid deflection channel.

8. The particle impact device in accordance with claim 1, wherein said deposition and deflection surface is recessed to define a fluid stagnation zone proximate thereto.

9. The particle impact device in accordance with claim 1 further comprising a multistage impactor.

10. A method of collecting a trace sample from an object for detection by a detector, said method comprising:
    directing a jet of fluid onto the object through a jet impingement port;

channeling a fluid stream including the trace sample through an intake port, the jet impingement port proximate the intake port, the jet impingement port and the intake port defining a substantially annular configuration;

directing the fluid stream and the trace sample toward a combined deposition and deflection apparatus;

impinging at least a portion of the trace sample on the combined deposition and deflection apparatus; and directing the fluid stream around the combined deposition and deflection apparatus.

11. The method in accordance with claim 10, wherein directing a jet of fluid onto the object comprises dislodging at least some trace particles from the object and entraining the at least some trace particles into the fluid stream.

12. The method in accordance with claim 11, wherein directing a jet of fluid onto the object comprises one of:
depressing a trigger device and directing a continuous jet of fluid during depression of the trigger device; and
directing a jet of fluid for a predetermined period as a function of a discrete jet initiation event.

13. The method in accordance with claim 10, wherein impinging at least a portion of the trace sample on the combined deposition and deflection apparatus comprises one of:
capturing at least a portion of the trace sample on a dosimeter film; and
capturing at least a portion of the trace sample on a heated porous material and at least partially vaporizing the at least a portion of the trace sample.

14. A hand-held trace particle detection system comprising:
a casing defining a slot;
a particle impact device comprising:
a first conduit defining an intake port defining a first transport area, said first conduit at least partially defining an air jet impingement port proximate said intake port, said air jet impingement port and said intake port defining a substantially annular configuration; and
a second conduit coupled to said first conduit, said second conduit defining a discharge port defining a second transport area, said first transport area greater than said second transport area; and
a combined deposition and deflection apparatus inserted into said slot and positioned downstream of said discharge port, said combined deposition and deflection apparatus defines a deposition and deflection surface positioned a predetermined distance from said discharge port, said deposition and deflection surface configured to deflect a fluid stream and collect at least a portion of particles entrained in the fluid stream.

15. The system in accordance with claim 14, wherein at least a portion of said deposition and deflection surface comprises at least one of:
a dosimeter film configured to capture the at least a portion of the particles; and
a porous material configured to be heated and at least partially vaporize the at least a portion of the particles.

16. The system in accordance with claim 14 further comprising at least one fluid transport apparatus, wherein:
said first conduit further at least partially defines an air jet impingement channel; and
said fluid transport apparatus is configured to direct a jet of fluid onto an object through said air jet impingement channel.

17. The system in accordance with claim 14 further comprising a housing extending about said combined deposition and deflection apparatus, wherein said combined deposition and deflection apparatus and said housing define a fluid deflection channel.

18. The system in accordance with claim 14, wherein said deposition and deflection surface is recessed to define a fluid stagnation zone proximate thereto.

19. The system in accordance with claim 14 further comprising a multistage impactor.

* * * * *